United States Patent
Francis et al.

(10) Patent No.: US 6,210,877 B1
(45) Date of Patent: Apr. 3, 2001

(54) PREDICTION OF CORONARY ARTERY DISEASE

(75) Inventors: Sheila E. Francis, Chesterfield; David C. Crossman; Gordon W. Duff, both of Sheffield, all of (GB)

(73) Assignee: Interleukin Genetics, Inc., San Antonio, TX (US)

( * ) Notice: Subject to any disclaimer, the term of this patent is extended or adjusted under 35 U.S.C. 154(b) by 0 days.

(21) Appl. No.: 08/813,456

(22) Filed: Mar. 10, 1997

(51) Int. Cl.$^7$ ............................. C12Q 1/68; C07H 21/04; C12P 19/34
(52) U.S. Cl. ..................... 435/6; 435/91.2; 536/23.5; 536/24.31; 536/24.33
(58) Field of Search ................................ 435/6, 91.2, 810; 536/23.5, 24.31, 24.33; 935/8, 78

(56) References Cited

U.S. PATENT DOCUMENTS

| | | | |
|---|---|---|---|
| 4,582,788 | 4/1986 | Erlich | 435/6 |
| 4,623,619 | 11/1986 | Owerbach et al. | 435/6 |
| 4,666,828 | 5/1987 | Gusella | 435/6 |
| 4,801,531 | 1/1989 | Frossard | 435/6 |
| 4,965,188 | 10/1990 | Mullis | 435/6 |
| 5,110,920 | 5/1992 | Erlich | 536/27 |
| 5,268,267 | 12/1993 | Smith | 435/6 |
| 5,554,509 | 9/1996 | Colucci | 435/6 |
| 5,658,729 | 8/1997 | Hayden et al. | 435/6 |
| 5,686,246 | 11/1997 | Kornman et al. | 435/6 |
| 5,698,399 | 12/1997 | Duff et al. | 435/6 |

OTHER PUBLICATIONS

Mansfield, J. et al., "Novel Genetic Association Between Ulcerative Colitis and the Anti–inflammatory Cytokine Interleukin–1 Receptor Antagonist", *Gastroenterology*, 106:637–642 (1994).
Alexander, *N.E.J.M.* 331(7): 468 (1994).
Anderson & Kin, *Am. Heart J.* 123(5): 1312 (1992).
Badimon, et al., *Circulation* 87: 3 (1993).
Clark, et al., *Nuc. Acids Res.* 14: 7897 (1986); Erratum in *Nuc. Acids Res.* 15(2): 868 (1987).
Clay et al., "Interleukin 1 receptor antagonist gene polymorphism association with lichen scleroses", *Hum. Genet.* 94:407–410 (1994).
Clay et al., "Novel interleukin–1 receptor antagonist exon polymorphisms and their use allele–specific mRNA assessment", *Human Genetics* 97(6):723–726 (Jun. 1996).
di Giovine et al., "Single base polymorphism at –511 in the human interluekin–1β gene (IL1β)", *Human Molecular Genetics* 1(6); 450 (1992).
Dinarello et al., "Anticytokine Strategies in the Treatment of the Systemic Inflammatory Response Syndrome", *JAMA* 269(4):1829–1835 (Apr. 1993).
Dinarello et al., "The Role of Interleukin–1 in Disease", *NEJM* 328(2):106–113 (Jan. 1993).
Duff, "Molecular Genetics of Cytokines", The Cytokine Handbook (1994) 2nd ed., Chap. 2: 21–30.
Galea, et al., *Ath. Thromb. Vasc. Biol.* 16: 1000 (1996).
Hasdai et al., "Increased serum concentrations of interleukin–1β in patients with coronary artery disease", *Heart* 76:24–28 (1996).
Knox, "Discovery may help battle heart attacks", *Houston Chronicle* (Jan. 10, 1996).
Liuzzo, et al., *N.E.J.M.* 331(7): 417 (1994).
Monro, *Lab Invest.* 58:249 (1988).
Nicklin, et al., *Genomics* 19: 382–4 (1994).
Tarlow et al., "Polymorphism in human IL–1 receptor antagonist gene intron 2 is caused by variable numbers of an 86–bp tandem repeat", *Hum. Genet.* 91:403–404 (1993).
Tarlow et al., "Severity of Alopecia Areata Is Associated with a Polymorphism in the Interleukin–1 Receptor Antagonist Gene", *J. Invest. Dermatol.* 103:387–390 (1994).

*Primary Examiner*—Carla J. Myers
(74) *Attorney, Agent, or Firm*—Foley, Hoag & Eliot LLP; Beth E. Arnold, Esq.; Anita Varma, Esq.

(57) ABSTRACT

Methods and assays are disclosed for predicting a patient's risk for an inflammatory disorder such as coronary artery disease or related vascular disorders. The methods comprise obtaining a biological sample from a patient and determining the presence or absence of a particular allele which is linked with coronary artery disease. Detection of the allele is indicative of susceptibility to develop coronary artery disease. Kits for the detection of coronary artery disease are additionally provided, as are means for identifying additional alleles associated with coronary artery disease.

15 Claims, No Drawings

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

CTCAGCAACA CTCCTAT                                                      17

(2) INFORMATION FOR SEQ ID NO:2:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:2:

TCCTGGTCTG CAGGTAA                                                      17

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

TGGCATTGAT CTGGTTCATC                                                   20

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

GTTTAGGAAT CTTCCCACTT                                                   20

PREDICTION OF CORONARY ARTERY DISEASE

BACKGROUND OF THE INVENTION

1. Field of the Invention

This invention relates to a presymptomatic assay for early identification of individuals more likely to develop coronary artery disease and related vascular disorders. The invention describes gene-specific, protein-specific, and epitope-specific probes and molecular genetic and biochemical assays.

2. Description of the Background

Coronary Artery Disease

Atherosclerosis (or arteriosclerosis) is the term used to describe progressive luminal narrowing and hardening of the arteries. This disease process can occur in any systemic artery in the human body. For example, atherosclerosis in the arteries that supply the brain can result in stroke. Gangrene may occur when the peripheral arteries are blocked, and coronary artery disease occurs when the arteries that supply oxygen and nutrients to the myocardium are affected.

Coronary artery disease is a multifactorial disease that results in the deposition of atheromatous plaque and progressive luminal narrowing of the arteries that supply the heart muscle. This plaque consists of a mixture of inflammatory and immune cells, fibrous tissue, and fatty material such as low-density lipids (LDL) and modifications thereof, and α-lipoprotein. The luminal narrowing or blockage results in reduced ability to deliver oxygen and nutrients to the heart muscle, producing myocardial infarction, angina, unstable angina, and sudden ischemic death as heart failure. Though occlusion usually progresses slowly, blood supply may be cut off suddenly when a portion of the built-up arterial plaque breaks off and lodges somewhere in an artery to block it temporarily, or more usually, when thrombosis occurs within the arterial lumen. Depending on the volume of muscle distal to the blockage during such an attack, a portion of myocardial tissue may die, weakening the heart muscle and often leading to the death of the individual.

The causes and mechanisms of the atheromatous plaque buildup are not completely understood, though many theories exist. One theory on the pathogenesis of atherosclerosis involves the following stages: 1) endothelial cell dysfunction and/or injury, 2) monocyte recruitment and macrophage formation, 3) lipid deposition and modification, 4) vascular smooth muscle cell proliferation, and 5) synthesis of extracellular matrix. According to this theory, the initiation of atherosclerosis is potentially due to a form of injury, possibly from mechanical stress or from chemical stress. How the body responds to this injury then defines whether or not, and how rapidly, the injury deteriorates into an atherosclerotic lesion. This in turn can result in arterial luminal narrowing and damage to the heart tissue which depends on the blood flow of oxygen and nutrients.

Though recent improvements in cardiovascular care have improved the life expectancy of coronary artery disease patients, this has been primarily from improvements in lowering lipid levels, limitation of damage after it has occurred, surgical restoration of blood supply, the suppression of abnormal heart rhythms and prevention of re-infarction. Little improvement has occurred, however, in early prevention of the disease by early diagnosis.

A key problem in treating coronary artery disease is proper diagnosis. Often the first sign of the disease is sudden death due to myocardial ischemia or myocardial infarction. Approximately half of all individuals who die of coronary artery disease die suddenly. Furthermore, for 40–60% of the patients who are eventually diagnosed as having coronary artery disease, myocardial infarction is the first presentation of disease. Unfortunately, approximately 40% of those initial events go unnoticed by the patient. For various reasons, the perception of symptoms by the patient does not correlate well with the total burden of coronary artery disease (Anderson & Kin, *Am. Heart J*. 123(5);1312–23 (1992)).

While the causes of atherosclerosis remain unknown, the proper diagnosis of susceptibility may provide patients sufficient time to reduce their risk of developing coronary artery disease. One method to reduce the risk of coronary artery disease is through alteration of patient lifestyle such as smoking cessation, exercise, weight loss, and stress reduction. Other methods include pharmaceutical intervention to treat hypertension, hypercholesterolemia, and diabetes, as well as the use of aspirin. Finally, genetic therapy promises to treat those rare genetic traits that result in a family history of cardiovascular disease (e.g., altered apolipoprotein metabolism).

The ability to identify high-risk individuals would allow physicians to focus preventive measures on those individuals who may gain the greatest benefit, and would provide strong incentives for those at risk to comply with such approaches.

Correlation of Coronary Artery Disease with Inflammatory Response

Evidence has accumulated to show that coronary artery disease and related vascular disorders may be initiated as a response to some form of injury in the arterial endothelium. The injury may be subtle, or may involve outright endothelial cell denudation. Focal sites of injury lead to increased permeability to plasma constituents and permit blood platelets and monocytes to adhere to endothelial or subendothelial connective tissue. Inflammatory factors released from activated platelets or monocytes then cause migration of smooth muscle cells from the media into the intima, followed by proliferation of these cells. Synthesis of extracellular matrix components by smooth muscle cells leads to accumulation of collagen, elastic fibers and proteoglycans. Monocytes also enter the intima, transform into macrophages, accumulate lipids and contribute to the evolution of the lesion. Single or short-lived injurious events are followed by regeneration of endothelial cells, restoration of endothelial function, and healing of the lesion. However, an abnormal inflammatory event may result in the development of an atheromatous plaque.

For many years epidemiologic studies have indicated that an individual's genetic composition is a significant risk factor for development of coronary artery disease. A family history of heart disease is associated with an increased individual risk of developing coronary artery disease. Lipid and cholesterol metabolism have historically been considered the primary genetic influence on coronary artery disease. For example, deficiency in cell receptors for low-density lipids (LDL), such as in familial hypercholesterolemia, is associated with high levels of plasma LDL and premature development of atherosclerosis (Brown & Goldstein, *Sci*. 191(4223); 150–4 (1976)).

Inflammation is now generally regarded as an important component of the pathogenic process of atherosclerosis (Munro, *Lab Invest*. 58: 249–261 (1988), Badimon, et al., *Circulation* 87: 3–16 (1993), Liuzzo, el al., *N.E.J.M*. 331(7):

417–24 (1994), Alexander, *N.L.J.M.* 331(7): 468–9 (1994)). Damage to endothelial cells that line the vessels leads to an accumulation of inflammatory cytokines, including IL-1, TNFα, and the release of prostanoids and growth factors such as prostaglandin $I_2$ ($PGI_2$), platelet-derived growth factor (PDGF), basic Fibroblast growth factor (bFGF), and granulocyte-monocyte cell stimulating factor (GM-CSF). These factors lead to accumulation and regulation of inflammatory cells, such as monocytes, that accumulate within the vessel walls. The monocytes then release additional inflammatory mediators, including IL-1, TNF, prostaglandin $E_2$ ($PGE_2$), bFGF, and transforming growth factors α and β (TGFα, TGFβ). All of these inflammatory mediators recruit more inflammatory cells to the damaged area, regulate the behavior of endothelial and smooth muscle cells and lead to the accumulation of atheromatous plaques.

Several inflammatory products, including IL-1β, have been identified in atherosclerotic lesions or in the endothelium of diseased coronary arteries (Galea, et al., *Ath. Thromb. Vasc. Biol.* 16:1000–6 (1996)). Also, serum concentrations of IL-1β are elevated in patients with coronary disease (Hasdai, et al., *Heart* 76: 24–8 (1996)). Although it was historically believed that the presence of inflammatory agents was responsive to injury or monocyte activation, it is also possible that an abnormal inflammatory response may be causative of coronary artery disease or create an increased susceptibility to the disease. Thus, the cytokines IL-1 and TNF, implicated in such an inflammatory reaction, may determine in part an individual's risk of coronary artery disease.

Genetics of the IL-1 Gene Cluster

The IL-1 gene cluster is on the long arm of chromosome 2 (2q13) and contains at least the genes for IL-1α (IL-1A), IL-1β (IL-1B), and the IL-1 receptor antagonist (IL-1RN), within a region of 430 Kb (Nicklin, et al., *Genomics* 19; 382–4 (1994)). The agonist molecules, IL-1α and IL-1β, have potent pro-inflammatory activity and are at the head of many inflammatory cascades. Their actions, often via the induction of other cytokines such as IL-6 and IL-8, lead to activation and recruitment of leukocytes into damaged tissue, local production of vasoactive agents, fever response in the brain and the hepatic acute phase response. All three IL-1 molecules bind to type I and to type II IL-1 receptors, but only the type I receptor transduces a signal to the interior of the cell. In contrast, the type II receptor is shed from the cell membrane and acts as a decoy receptor. The receptor antagonist and the type II receptor, therefore, are both anti-inflammatory in their actions.

Inappropriate production of IL-1 plays a central role in the pathology of many autoimmune and inflammatory diseases, including rheumatoid arthritis, inflammatory bowel disorder, psoriasis, and others. In addition, there are stable inter-individual differences in the rates of production of IL-1, and some of this variation may be accounted for by genetic differences at IL-1 gene loci. Thus, the IL-1 genes are reasonable candidates for determining part of the genetic susceptibility to inflammatory diseases, most of which have a multifactorial etiology with a polygenic component. Indeed, there is increasing evidence that certain alleles of the IL-1 genes are over represented in these diseases.

Genetic Diagnosis

Traditional methods for the diagnosis of heritable diseases have depended on either the identification of abnormal gene products (e.g., sickle cell anemia) or an abnormal phenotype (e.g., mental retardation). These methods are of limited utility for heritable diseases with late onset and no easily identifiable phenotypes, such as, for example, Alzheimer's disease. With the development of genetic testing, it is now possible to identify gene mutations which indicate a propensity to develop disease, even when the disease is of polygenic origin. The number of diseases that can be diagnosed by molecular biological methods continues to grow with increased understanding of the genetic basis of multifactorial disorders (see e.g., U.S. Pat. Nos. 4,582,788; 5,110,920; 4,801,531; 4,666,828; and 5,268,267).

Genetic testing (also called genetic screening, genotyping or molecular diagnostics) can be defined broadly as the testing of nucleic acid of a patient in an analytical capacity to determine if a patient contains mutations (or alleles or polymorphisms) that either cause a disease state or are "linked" to the mutation causing a disease state. Linkage refers to the phenomenon that DNA sequences which are close together in the genome have a tendency to be inherited together. Two sequences may also be linked because of some selective advantage of co-inheritance.

The early detection of a predisposition to genetic diseases presents the best opportunity for medical intervention. Early genetic diagnosis may improve the prognosis for a patient through supervision and early intervention before the clinically detectable disorder occurs. In cases where patients with similar symptoms are treated with variable success, sophisticated genetic testing can differentiate individual patients with subtle or undetectable differences and can lead to more suitable individual treatments. It is even possible that early intervention may one day involve methods such as gene therapy.

SUMMARY OF THE INVENTION

The present invention provides a novel method for the early detection of a propensity to develop coronary artery disease and related vascular disorders. It also provides kits for the early detection of said propensity and methods for identifying additional alleles associated with this disease.

Generally, the method of predicting increased risk for coronary artery disease consists of detecting the presence of at least one copy of an allele selected from the group consisting of IL-1RN allele 2 and IL-1B allele 2. Having one or more of these alleles indicates increased risk for coronary artery disease. Detecting alleles may be performed directly, by analyzing the DNA from the IL-1 region, or indirectly, by analyzing the RNA or protein products of the DNA.

In another embodiment, the invention can be described as the following: isolating nucleic acid from the patient, identifying one or more alleles present in the IL-1 gene cluster, and comparing the one or more alleles to a control sample. The control sample contains at least one allele from the IL-1 gene cluster known to be associated with coronary artery disease. In a preferred embodiment, the control sample contains the IL-1 RN (VNTR) allele 2 and/or the IL-1B (−511) allele 2. Similarity of the identified alleles from the patient to the control sample indicates the patient's predisposition to coronary artery disease.

Another embodiment of the invention is a kit for the detection of an allele that is predictive of coronary artery disease. The kit generally includes at least one oligonucleotide complementary to a DNA sequence in the IL-1 gene family; and a control sample. The control sample is an allele known to be associated with coronary artery disease, as above. The kit may also include a DNA sampling means, a DNA purification means, and PCR reagents. Further, the oligonucleotide may contain a detectable label.

Another embodiment of the invention provides a method of identifying alleles associated with coronary artery disease. The method consists of gathering a first cohort of patients without coronary artery disease, gathering a second cohort of patients with coronary artery disease (as determined by angiographic evidence) and identifying the IL-1 alleles present in the first and second cohorts. The allele that is over represented in the second cohort as compared with the first cohort is identified as associated with coronary artery disease.

Other embodiments and advantages of the invention are set forth in part in the description which follows, and will be obvious from this description, or may be learned from the practice of the invention.

DETAILED DESCRIPTION OF THE PREFERRED EMBODIMENTS

As embodied and broadly described herein, the present invention is directed to methods for predicting a patient's propensity toward developing coronary artery disease and to diagnostic kits, oligonucleotide probes and other reagents that can be used with these methods. The invention is also directed to a method for identifying genetic markers associated with coronary artery disease.

As used herein, the phrase coronary artery disease refers to disorders and conditions generally recognized by those skilled in the art as related to the deposition of atheroma in the large- and medium-sized arteries serving the heart. Thus, coronary artery disease means clinical syndromes (including, but not limited to, angina, myocardial infarction, unstable angina, and sudden ischemic death) which are based on the pathology of coronary artery atheroma.

The term marker is meant to describe regions of the DNA that vary between individuals. For example, the 'VNTR' marker from the IL-1RN gene is described herein. The different sequence variants at a given marker are called alleles or polymorphisms. The VNTR marker has at least five different alleles, three of which are rare. Different alleles could have a single base change, including a substitution, insertion or deletion, or could have a change that affects multiple bases, including substitutions, insertions, deletions, repeats, inversions and combinations thereof. Alleles can be directly detected in the DNA of an individual, or indirectly detected in the RNA or protein.

As used herein, the process of detecting alleles is variously described as genotyping, determining or identifying an allele or polymorphism, or any similar phrase. The allele actually detected might be a disease-causing mutation, or a mutation that is linked to a disease-causing mutation.

The terms IL-1 gene cluster or IL-1 loci as used herein include all the nucleic acid at or near the 2q13 region of chromosome 2, including at least the IL-1A, IL1B and IL-1RN genes and any other linked sequences.

The term IL-1 RN (HVTR) allele 2 describes allele 2 of the VNTR marker of the IL-1 RN gene. This allele is characterized by having two copies of the VNTR repeat and produces a 240 bp product when amplified with the primers described herein.

The term IL-1B (−511) allele 2 describes allele 2 of the −511 marker of the IL-1B gene. This allele contains a Bsu361 site and produces 190 and 114 bp fragments when amplified with the primers described herein and digested with Bsu361.

By propensity or predisposition or susceptibility to disease what is meant is that certain alleles are hereby discovered to be associated with a given disease state. They are thus over represented in individuals with disease as compared with healthy individuals. Therefore, the presence of such alleles indicates that an individual is at risk for the disease.

The invention is directed to a method of predicting the propensity or predisposition of a patient to coronary artery disease by genotyping the patient's DNA at the IL-1 loci. The patient's genotype is compared with a control sample that contains one or more IL-1 allelic variants which are known to correlate with or be associated with the disease state. Control samples may contain the IL-1RN allele 2 and/or the IL-1B allele 2 and linked alleles, or other alleles identified as per the methods described herein. The alleles in the control sample may be in the form of genomic or cloned DNA sequences from the IL-1 gene cluster or may contain the end products appropriate for the assay format employed. For example, where the assay involves monoclonal detection of specific epitopes, the control samples might comprise the epitopes or proteins corresponding to the described alleles.

Techniques for determining the presence of particular markers may be nucleic acid techniques based on hybridization, size, or sequence, such as restriction fragment length polymorphism (RFLP) or nucleic acid sequencing.

These techniques may also comprise the step of amplifying the nucleic acid before analysis. Amplification techniques are known to those of skill in the art and include cloning, polymerase chain reaction (PCR), polymerase chain reaction of specific alleles (PASA), polymerase chain ligation, nested polymerase chain reaction, and the like. Amplification products may be assayed in a variety of ways, including size analysis, restriction digestion followed by size analysis, detecting specific tagged oligonucleotide primers in the reaction products, allele-specific oligonucleotide (ASO) hybridization, sequencing, and the like.

Alternatively, allele detection techniques may be protein based if a particular allele produces a protein with an amino acid variant. For example, epitopes specific for the amino acid variant can be detected with monoclonal antibodies.

The invention is also directed to methods for identifying additional IL-1 alleles linked to a propensity to develop coronary artery disease. The IL-1 alleles present in diseased patients are compared with those present in non-diseased patients to determine if any allele is over represented in the diseased patients. Alleles can be the existing known IL-1 alleles, or additional markers can be identified by any of the techniques known in the art, including DNA sequencing of the region near these genes.

Another embodiment of the invention is directed to diagnostic kits for detecting a propensity for coronary artery disease in a patient. The kits can be used presymptomatically or prenatally. The diagnostic kit may comprise one or more oligonucleotides capable of hybridizing to nucleic acid from the IL-1 gene cluster. A number of assay formats are useful for genotyping using the provided oligonucleotides. The most common formats involve nucleic acid binding, such as, for example, to filters, beads, or microtiter plates and the like. Techniques involved include dot blots, RNA blots, DNA blots, PCR, RFLP, and the like.

The oligonucleotides may be a variety of natural and synthetic compositions such as, for example, synthetic oligonucleotides, restriction fragments, cDNAs, synthetic PNAs (protein nucleic acids), and the like. The assay may also employ labeled oligonucleotides to allow ease of identification in the assays. Examples of labels which may be employed include radiolabels, enzymes, florescent compounds, streptavidin, avidin, biotin, magnetic moieties, metal binding moieties, antigen or antibody moieties, and the like.

The kit may also include DNA sampling means such as the AmpliCard™ (University of Sheffield, Sheffield, England S10 2JF), also described in Tarlow J W, et al. Journal of Investigative Dermatology 1994: 103: 387–389, incorporated by reference herein. Other suitable DNA sampling means include DNA purification means and PCR reagents, such as 10X reaction buffers, thermostable polymerase, and/or dNTPs.

The following example illustrates embodiments of the invention, but should not be viewed as limiting the scope of the invention.

EXAMPLE 1.

Markers for Single Vessel Coronary Artery Disease

The objective of this study was to determine if patients with an early form of coronary artery atherosclerosis, i.e., single vessel coronary artery disease, were more likely to have specific alleles in the following genes: IL-1A (−889 marker), IL-1B (−511 and +3953 markers), IL-1 RN (VNTR marker) or TNFα (−308 marker). Multiple vessel disease generally represents a later stage of disease that may involve many factors which could complicate data interpretation. Therefore, patients who presented with a complaint of chest pain were evaluated by a cardiologist, and those with angiographic evidence of significant atherosclerosis in more than one coronary artery were excluded from analysis.

Patient Cohorts: Angiography from either the femoral or brachial artery was performed using conventional techniques. Of the patients examined, eighty-five (85) had no obvious luminal irregularities by angiography and were classified as controls having angiographically normal coronary arteries. A patient was classified as having single vessel disease if one of three epicardial coronary vessels contained an epicardial stenosis causing >50% reduction in luminal diameter, as assessed by eye. Fifty-eight (58) patients were found to have single vessel coronary artery disease. Patients with multiple vessel disease were excluded. Both control and single vessel disease groups had comparable mean ages, 57.6+10.4 years and 56.4+9.4 years, respectively. The male to female ratio in the control group was 1 to 1.7 and 2.6 to 1 in the diseased group.

General Methods: Reactions and manipulations involving nucleic acid techniques, unless stated otherwise, were performed as generally described in Sambrook, et al., *Molecular Cloning: A Laboratory Manual*, Cold Spring Harbor Laboratory Press (1989). Polymerase chain reaction (PCR) was carried out generally as described in *PCR Protocols: A Guide to Methods and Applications*, Academic Press, San Diego, Calif. (1990). Genotyping methodology was as generally described in U.S. Pat. Nos. 4,666,828; 4,683,202; 4,801,531; 5,192,659; and 5,272,057 and McDowell, et al., *Arthritis & Rheumatism* 38(2): 221–8 (1995).

DNA preparation: DNA was extracted from whole blood using a modification of the salt-out method (Nucleon II™, Scotlab, UK).

Genotyping IL-1RN: Alleles associated with the IL-1RN gene were previously described by Tarlow, et al., *Human Genetics* 91:403–4 (1993). Enzymes used in PCR were from Promega (UK) and thermocyclers were either MJ Research DNA Engine or Biometra. The following primers were produced in an ABI DNA synthesizer:

5' CTCAGCAACACTCCTAT 3' (SEQ ID No: 1)

5' TCCTGGTCTGCAGGTAA 3' (SEQ ID No: 2)

PCR amplification was performed with a final magnesium concentration of 1.75 mM and a cycling protocol of 1 cycle at 96° C. for 1 minute; 30 cycles of [94° C. for 1 minute, 60° C. for 1 minute, and 70° C. for 1 minute]; and 1 cycle at 70° C. for 2 minutes. Following PCR the different alleles were electrophoresed on a 2% agarose gel stained with ethidium bromide and visualized and identified under uv light. Negative controls without DNA were performed in each experiment.

Intron 2 of the IL-1 RN gene contains a variable number tandem repeat (VNTR) region that gives rise to five (5) alleles as follows:

Allele 1 contains four repeats and displays a 412 bp PCR product;

Allele 2 contains two repeats and displays a 240 bp PCR product;

Allele 3 contains three repeats and displays a 326 bp PCR product;

Allele 4 contains five repeats and displays a 498 bp PCR product; and

Allele 5 contains six repeats and displays a 584 bp PCR product.

Genotyping IL-1B (−511)

The −511 marker of IL-1B was described by di Giovine, *Hum. Molec. Genet.* 1(6):450 (1992). The single base variation (C/T) marker at IL-1B base −511 was identified on the basis of an AvaI site on allele 1 (C), and a Bsu361 site on allele 2 (TF). PCR was performed with 1 cycle at 95° C. for 2 minutes, 35 cycles at [95° C. for 1 minute, 53° C. for 1 minute, and 74° C. for 1 minute] and 1 cycle at 74° C. for 4 minutes. Analysis of the PCR products was by restriction enzyme digestion with Aval and Bsu361 at 37° C. for 8 hours followed by size analysis with 8% PAGE. Che following primers were produced in an ABI DNA synthesizer (Clark, el al., *Nucl. Acids Res.* 14:7897–7914 (1986) [published erratum appears in *Nucleic Acids Res.* 15(2):868 (1987)], GENBANK X04500):

```
5' TGGCATTGATCTGGTTCATC 3'    (-702/-682)   (SEQ ID NO: 3)

5' GTTTAGGAATCTTCCCACTT 3'    (-417/-397)   (SEQ ID NO: 4)
```

Results: There was no significant difference between the control and diseased patients in the frequency of different alleles in the genes for IL-1 A (−889 marker), IL-1B (+3953 marker) or TNFα (−308 marker). However, allele 2 of the VNTR marker in the IL-1RN gene was significantly over represented in the single vessel disease patients, 41% versus 22% in controls. It is estimated that individuals with at least one copy of allele 2 are 2.44 times as likely to have single vessel coronary artery disease than those who are negative for allele 2 (Odds Ratio=2.44, p=0.003, 95% confidence interval=1.35–4.43).

In addition, individuals who had two copies, i.e., were homozygous for allele 2 in IL-1RN , were 5.36 times as likely to have single vessel coronary artery disease than those who were negative for allele 2 (Odds Ratio=5.36, p=0.005, 95% confidence interval=1.6–17.97).

Carriage of one copy of allele 2 of the −511 marker of the IL-1B gene was increased in single vessel coronary disease to 52% compared with 38% in controls. It is estimated that individuals with at least one copy of allele 2 are 1.74 times as likely to have single vessel disease than those who are negative for allele 2 (Odds ratio=1.74, p=0.1, 95% confidence interval=0.86–3.52). This finding is not quite significant, however, the small sample size limited the study.

These findings indicate that allele 2 of the IL-1RN gene is a marker for susceptibility to the development of coronary artery atherosclerosis. This allele is associated with an increased risk of coronary artery disease of 2.4 to 5.4 times, depending on whether there is one copy (heterozygous) or two copies (homozygous) of the disease-associated allele. The influence of this allele on risk for coronary artery disease is shown in Table 1 relative to other common risk factors.

Additionally, an allele for the IL-1B gene was discovered to be associated with single vessel coronary artery disease. This allele is associated with an increased risk of coronary artery disease of 1.74 times.

TABLE 1

| Risk Factor | Increased Risk for Coronary Artery Disease |
| --- | --- |
| Smoking 1 pack/day | 2.5 |
| Sedentary lifestyle | 1.9 |
| Severe obesity-women | 3.3 |
| Hypertension | 2.1 |
| High cholesterol (>240) | 2.4 |
| IL-1RN (VNTR) allele 2-heterozygous | 2.4 |
| IL-1RN (VNTR) allele 2-homozygous | 5.4 |
| IL-1B (-511) allele 2 | 1.74–1.92 |

EXAMPLE 2.

Markers for Multiple Vessel Coronary Artery Disease

The objective of this study was to determine if patients with a later or more diffuse form of coronary artery atherosclerosis, i.e., multiple vessel coronary artery disease, were more likely to have specific alleles in the genes of the IL-1 gene cluster or TNFα.

Patient Cohorts: Patient cohorts were determined as in Example 1, except that a patient was classified as having multiple vessel disease if more than one epicardial coronary vessel contained an epicardial stenosis causing >50% reduction in luminal diameter, as assessed by eye. Of the patients examined, 86 were classified as controls having angiographically normal coronary arteries and 315 patients were found to have multiple vessel coronary artery disease. Both control and single vessel disease groups had comparable mean ages, 57.6±10.4 years and 60.8±1.13 years, respectively. The male to female ratio in the control group was 1:1.7 and 3.7:1 in the diseased group.

General Methods: Reactions and methods were as in Example 1.

Results: There was no significant difference between the control and diseased patients in the frequency of different alleles in the genes for IL-1A (−889 marker), IL-1B (+3953 marker), and IL-1RN (VNTR marker). However, carriage of one copy of the Bsu361 allele (allele 2) of the −511 marker of the IL-1B gene was increased in the multiple vessel disease patients, 54% versus 38% in controls. It is estimated that individuals with at least one copy of allele 2 of the −511 marker are 1.92 times as likely to have multiple vessel coronary artery disease than those who are negative for allele 2 (Odds Ratio=1.92, p=0.009, 95% confidence interval=1.17–3.16). There appears to be no dose effect, in this population at least, for the −511 marker.

In summary, an allele for the IL-1B gene was discovered to be associated with multiple vessel coronary artery disease. This allele is associated with an increased risk of coronary artery disease of 1.92 times.

Single vessel and multiple vessel coronary artery disease appear to be each linked with different genes of the IL-1 gene cluster. This may arise as a true biological distinction, where IL-1 ra modulates IL-1β effects in such a way as to produce the single vessel phenotype. Alternatively, it may be that both genes are in fact associated with coronary artery disease as a whole and that the associations observed here result from the way this particular population exhibited coronary artery disease. With either interpretation, a strong association between IL-1 biology and coronary artery disease has been established.

Other embodiments and uses of the invention will be apparent to those skilled in the art from consideration of the specification and practice of the invention disclosed herein. All references cited herein, for whatever reason, are specifically incorporated by reference. The specification and examples should be considered exemplary only with the true scope and spirit of the invention suggested by the following claims.

What is claimed is:

1. A method for determining a patient's predisposition to coronary artery disease, comprising:
   a. detecting a first allele from the IL-1 loci of a patient; and
   b. comparing the first allele to a second allele,
     i. wherein the second allele is selected from the group consisting of IL1-RN (VNTR) allele 2 and IL-1B (−511) allele 2; and
     ii. wherein said patient is predisposed to coronary artery disease if the first allele is identical to the second allele.

2. The method of claim 1, wherein detecting the first allele comprises RFLP analysis of a nucleic acid.

3. The method of claim 1, wherein detecting the first allele comprises amplification of a nucleic acid.

4. A method for determining a patient's predisposition to coronary artery disease, comprising:
   a. isolating a DNA from a patient;
   b. analyzing said DNA to determine a first allele; and
   c. comparing said first allele with a second allele, wherein the second allele selected from the group consisting of IL1-RN (VNTR) allele 2 and IL-1B (−511) allele 2 and wherein said patient is predisposed to coronary artery disease if the first allele is identical to the second allele.

5. The method of claim 4, wherein said DNA is analyzed by:
   a. amplifying the DNA in a polymerase chain reaction to produce an amplification product; and
   b. size fractionation of the amplification product.

6. The method of claim 5, wherein the polymerase chain reaction is performed with one or more oligonucleotides selected from the group consisting of:

5' CTCAGCAACACTCCTAT 3'    (SEQ ID No: 1);

5' TCCTGGTCTGCAGGTAA 3'    (SBQ ID No: 2);

5' TGGCATTGATCTGGTTCATC 3'    (SEQ ID NO: 3);

and

5' GTTTAGGAATCTTCCCACTT 3'    (SEQ ID NO: 4).

7. The method of claim 6, wherein said one or more oligonucleotides are detectably labeled.

8. A method of determining a patient's propensity for coronary artery disease, comprising:
   a. typing a patient's nucleic acid at the IL-1 loci to determine a genotype; and wherein having either IL1-RN (VNTR) allele 2 and IL-1B (−511) allele 2 indicates an increased propensity for coronary artery disease.

9. A method as in claim 8, wherein said coronary artery disease is single vessel coronary artery disease and said genotype is IL-1RN (VNTR) allele 2.

10. A method as in claim 8, wherein said coronary artery disease multiple vessel coronary artery disease and said genotype is IL-1B (−511) allele 2.

11. A method of predicting increased propensity for coronary artery disease in a patient, comprising:
   detecting in a patient the presence of at least one copy of an allele selected from the group consisting of IL-1RN allele 2 and IL-1B allele 2,
   wherein detecting said allele indicates that said patient has an increased propensity for coronary artery disease.

12. A method of identifying alleles associated with coronary artery disease, comprising:
   a. gathering a first cohort of patients without coronary artery disease;
   b. gathering a second cohort of patients with coronary artery disease;
   c. detecting an allele of the IL-1 gene cluster from the first and second cohorts; and
   d. identifying said allele which is over-represented in the second cohort as compared with the first cohort wherein said allele is associated with coronary artery disease.

13. The method of claim 11, wherein detecting more than one copy of said allele indicates a higher propensity for coronary artery disease than detecting one copy of said allele.

14. The method of claim 3, wherein the amplification is PCR amplification.

15. The method of claim 14, wherein the PCR amplification is performed with a PCR primer selected from the group consisting of:

```
5'CTCAGCAACACTCCTAT 3'       (SEQ ID No. 1);
5'TCCTGGTCTGCAGGTAA 3'       (SEQ ID No. 2);
5'TGGCATTGATCTGGTTCATC 3'    (SEQ ID No: 3);
and
5'GTTTAGGAATCTTCCCACTT 3'    (SEQ ID No: 4).
```

* * * * *